United States Patent
Thomas et al.

(10) Patent No.: US 12,266,111 B2
(45) Date of Patent: Apr. 1, 2025

(54) VISUALIZATION OF SUB-PLEURAL REGIONS

(71) Applicant: Vida Diagnostics, Inc., Coralville, IA (US)

(72) Inventors: Benj Thomas, Eden Prairie, MN (US); Samuel Peterson, Topanga, CA (US); John D. Newell, Jr., Port Townsend, WA (US)

(73) Assignee: Vida Diagnostics, Inc., Coralville, IA (US)

( * ) Notice: Subject to any disclaimer, the term of this patent is extended or adjusted under 35 U.S.C. 154(b) by 337 days.

(21) Appl. No.: 17/534,503

(22) Filed: Nov. 24, 2021

(65) Prior Publication Data

US 2022/0172367 A1    Jun. 2, 2022

Related U.S. Application Data

(60) Provisional application No. 63/118,808, filed on Nov. 27, 2020.

(51) Int. Cl.
*G06T 7/00* (2017.01)
*A61B 6/50* (2024.01)
(Continued)

(52) U.S. Cl.
CPC .............. *G06T 7/0016* (2013.01); *A61B 6/50* (2013.01); *G06F 18/2413* (2023.01); *G06T 7/50* (2017.01);
(Continued)

(58) Field of Classification Search
CPC .......... A61B 6/50; A61B 6/5211–5223; G06T 7/0012; G06T 7/11; G06T 7/12;
(Continued)

(56) References Cited

U.S. PATENT DOCUMENTS

| | | |
|---|---|---|
| 5,558,091 A | 9/1996 | Acker et al. |
| 6,380,732 B1 | 4/2002 | Gilboa |

(Continued)

FOREIGN PATENT DOCUMENTS

| | | |
|---|---|---|
| CN | 1395713 A | 2/2003 |
| DE | 102005039657 A1 | 3/2007 |

(Continued)

OTHER PUBLICATIONS

Machine translation of Iwasawa et al. (WO 2017/150497 A1, Sep. 8, 2017).*

(Continued)

*Primary Examiner* — Carolyn A Pehlke
(74) *Attorney, Agent, or Firm* — Fredrikson & Byron, P.A.

(57) ABSTRACT

A method for visualizing sub-pleural regions of an anatomical structure of interest from a set of volumetric data includes receiving the set of volumetric data representative of the anatomical structure. The anatomical structure can comprise an outer surface and a plurality of sub-pleural regions with each of the plurality of sub-pleural regions being a region of the anatomical structure which is distant from the outer surface by a corresponding sub-pleural depth. The method further includes determine a first sub-pleural region of the anatomical structure of interest and extracting, from the set of volumetric data, the portions of volumetric data representative of the first sub-pleural region. The method also includes rendering a display image based upon the first sub-pleural region and the extracted volumetric data.

20 Claims, 20 Drawing Sheets

(51) Int. Cl.
  *G06F 18/2413* (2023.01)
  *G06T 7/50* (2017.01)
(52) U.S. Cl.
  CPC .............. *G06T 2207/20081* (2013.01); *G06T 2207/20092* (2013.01); *G06T 2207/30061* (2013.01)
(58) Field of Classification Search
  CPC . G06T 2207/30004; G06T 2207/30061; G06T 2207/10081
  See application file for complete search history.

(56) References Cited

U.S. PATENT DOCUMENTS

| | | |
|---|---|---|
| 6,456,868 B2 | 9/2002 | Saito et al. |
| 6,466,687 B1 | 10/2002 | Uppaluri et al. |
| 6,466,815 B1 | 10/2002 | Saito et al. |
| 6,558,333 B2 | 5/2003 | Gilboa et al. |
| 6,580,938 B1 | 6/2003 | Acker |
| 6,615,155 B2 | 9/2003 | Gilboa |
| 6,711,429 B1 | 3/2004 | Gilboa et al. |
| 6,775,404 B1 | 8/2004 | Pagoulatos et al. |
| 6,807,292 B1 | 10/2004 | Goto et al. |
| 7,233,820 B2 | 6/2007 | Gilboa |
| 7,274,810 B2 | 9/2007 | Reeves et al. |
| 7,338,452 B2 | 3/2008 | Shiina et al. |
| 7,611,452 B2 | 11/2009 | Allison et al. |
| 7,711,167 B2 | 5/2010 | Kiraly et al. |
| 7,760,941 B2 | 7/2010 | Bornemann et al. |
| 8,045,769 B2 | 10/2011 | Wiemker et al. |
| 8,219,179 B2 | 7/2012 | Ganatra et al. |
| 8,428,317 B2 | 4/2013 | Kimia et al. |
| 8,611,989 B2 | 12/2013 | Roberts |
| 8,700,132 B2 | 4/2014 | Ganatra et al. |
| 9,076,201 B1 | 7/2015 | Negahdar et al. |
| 11,176,666 B2 | 11/2021 | Peterson et al. |
| 2003/0029464 A1 | 2/2003 | Chen et al. |
| 2003/0051733 A1 | 3/2003 | Kotmel et al. |
| 2003/0108853 A1 | 6/2003 | Chosack et al. |
| 2005/0182295 A1 | 8/2005 | Soper et al. |
| 2005/0228250 A1 | 10/2005 | Bitter et al. |
| 2005/0251017 A1 | 11/2005 | Azar |
| 2005/0272971 A1 | 12/2005 | Ohnishi et al. |
| 2006/0030958 A1 | 2/2006 | Tschirren et al. |
| 2007/0003124 A1 | 1/2007 | Wood et al. |
| 2007/0053562 A1 | 3/2007 | Reinhardt et al. |
| 2007/0078334 A1 | 4/2007 | Scully et al. |
| 2007/0092864 A1 | 4/2007 | Reinhardt et al. |
| 2007/0223794 A1 | 9/2007 | Preiss et al. |
| 2007/0293721 A1 | 12/2007 | Gilboa |
| 2008/0205722 A1 | 8/2008 | Schaefer et al. |
| 2010/0305463 A1 | 12/2010 | Macklem et al. |
| 2011/0071404 A1 | 3/2011 | Schmitt et al. |
| 2012/0249546 A1 | 10/2012 | Tschirren et al. |
| 2012/0284657 A1 | 11/2012 | Hafey et al. |
| 2014/0105472 A1 | 4/2014 | Yin et al. |
| 2014/0275952 A1 | 9/2014 | Monroe et al. |
| 2015/0238270 A1 | 8/2015 | Raffy et al. |
| 2015/0332454 A1 | 11/2015 | Yin et al. |
| 2015/0351714 A1 | 12/2015 | De Backer |
| 2017/0124771 A1 | 5/2017 | Canfield et al. |
| 2017/0278301 A1 | 9/2017 | Peterson et al. |
| 2019/0131012 A1* | 5/2019 | Osawa ................. G06V 10/764 |
| 2019/0290225 A1 | 9/2019 | Dunican et al. |
| 2020/0085382 A1* | 3/2020 | Taerum ................. G06T 7/0016 |
| 2021/0166382 A1* | 6/2021 | Kanada ................. G06T 7/0012 |
| 2021/0183054 A1 | 6/2021 | Guo et al. |
| 2021/0312616 A1 | 10/2021 | Thomas et al. |

FOREIGN PATENT DOCUMENTS

| | | |
|---|---|---|
| JP | H11318884 A | 11/1999 |
| JP | 2004113537 A | 4/2004 |
| JP | 2004283373 A | 10/2004 |
| JP | 2010541114 A | 12/2010 |
| JP | 2014210084 A | 11/2014 |
| WO | 03007198 A2 | 1/2003 |
| WO | 03086498 A2 | 10/2003 |
| WO | 2005007023 A2 | 1/2005 |
| WO | 2005119505 A2 | 12/2005 |
| WO | 2009103046 A2 | 8/2009 |
| WO | WO-2017150497 A1 * | 9/2017 ............... A61B 6/03 |

OTHER PUBLICATIONS

The Lungs (www.teachmeanatomy.info/thorax/organs/lungs/, retrieved Apr. 4, 2024).*

Li, "Efficient Optimal Net Surface Detection for Image Segmentation—From Theory to Practice," M.Sc. Thesis, The University of Iowa, Dec. 2003.

Tschirren et al., "Intrathoracic airway trees: segmentation and airway morphology analysis from low-dose CT scans," IEEE Trans Med Imaging, vol. 12, Dec. 24, 2005, pp. 1529-1539.

Tschirren et al., "Matching and anatomical labeling of human airway tree," IEEE Trans Med Imaging, vol. 12, Dec. 24, 2005, pp. 1540-1547.

Tschirren, "Segmentation, Anatomical Labeling, Branchpoint Matching, and Quantitative Analysis of Human Airway Trees in Volumetric CT Images," Ph.D. Thesis, The University of Iowa, Aug. 2003.

Tschirren, "Segmentation, Branchpoint Matching, and Anatomical Labeling of Human Airway Trees in Volumetric CT Images," Slides from Ph.D. Thesis, The University of Iowa, Jul. 10, 2003.

Austin, "Pulmonary emphysema: imaging assessment of lung volume reduction surgery," Radiology, vol. 212, No. 1, Jul. 1999, pp. 1-3.

Auzinger et al., "Vessel Visualization using Curved Surface Reformation," IEEE Transaction on Visualization and Computer Graphics, vol. 19, No. 12, Dec. 1, 2013, pp. 2858-2867.

Brown et al., "CAD in clinical trials: Current role and architectural requirements," Available online at www.sciencedirect.com, Apr. 20, 2007, 6 pages.

Cetti et al., "Collateral ventilation," Thorax Journal, vol. 61, 2006, pp. 371-373.

"COPD Essentials for Health Professionals," Retrieved from: https://www.nhlbi.nih.gov/health/educational/copd/campaign-materials/html/providercard.htm on Aug. 18, 2014, 2 pages.

Frangi, A. et al., "Multiscale Vessel Enhancement Filtering," MIC-CAI 1998; 1496 (3), pp. 130-137.

Herth et al., "Efficacy Predictors of Lung Volume Reduction with Zephyr Valves in a European Cohort," European Respiratory Journal, vol. 39, No. 6, Jan. 26, 2012, pp. 1334-1342.

Herth, F.J.F. et al., "Endoscopic Lung Volume Reduction," Respiration, vol. 79, No. 1, 2010, pp. 5-13.

Herth et al., "Radiological and clinical outcomes of using Chartis to plan endobronchial valve treatment," European Respiratory Journal, electronic publication May 3, 2012, retrieved from <http://erj.ersjournals.com/content/41/2/302> on Sep. 30, 2014.

Horn, Berthold K. P., "Closed-form solution of absolute orientation using unit quartemions", Journal of the Optical Society of America A, Apr. 1987, pp. 629-642, vol. 4.

"InterVapor—How it Works," Uptake Medical, Retrieved online from <https://web.archive.org/web/20121124070645/http://www.uptakemedical.com/about-intervapor/how-it-works, dated Nov. 24, 2012, 3 pages.

Kanitsar et al., "Advanced Curved Planar Reformation," IEEE Visualization 2003, Seattle, Washington, Oct. 19-24, 2003, pp. 43-50.

Kanitsar, "Curved Planar Reformation for Vessel Visualization," Dissertation, 2004, 107 pages.

Kuhnigk, J-M. et al., "Lung lobe segmentation by anatomy-guided 3D watershed transform," Proceedings of SPIE Medical Imaging, vol. 4, 2003, pp. 1482-1490.

Leotta, Daniel F., "An Efficient calibration Method for Freehand 3-D Ultrasound Imaging Systems", May 13, 2004, pp. 999-1008, vol. 30, No. 7, Ultrasound in Medicine & Biology, (doi:10.1016/j.ultrasmedbio.2004.5.007).

(56) References Cited

OTHER PUBLICATIONS

Magnussen, H. et al., "Effect of fissure integrity on lung volume reduction using a polymer sealant* in advanced emphysema," Thorax, vol. 67, No. 4, 2012, pp. 302-308.

Mishima et al., "Complexity of terminal airspace geometry assessed by lung computed tomography in normal subjects and patients with chronic obstructive pulmonary disease," Proceedings of the National Academy of Sciences, vol. 96, No. 16, Aug. 3, 1999, pp. 8829-8834. Abstract only.

Mistelbauer et al., "Smart super views a knowledge-assisted interface for medical visualization", 2012 IEEE Conference on Visual Analytics Science and Technology, Oct. 14, 2012, pp. 163-172.

Nimura et al., "A study on quantifying COPD severity by combining pulmonary function tests and CT image analysis," Medical Imaging 2011: Computer-Aided Diagnosis, Mar. 3, 2011, 9 pages.

Noppen, Marc, "Collateral Ventilation in End-Stage Emphysema: a Blessing or a Curse for New Bronchoscopic Treatment Approaches (or Both)?" Respiration, vol. 74, No. 5, Jan. 2007, pp. 493-495.

Obuchowski, "ROC Analysis," American Journal of Roentgenology, vol. 184, Feb. 2005, pp. 364-372.

Odry et al., "Automated detection of mucus plugs within bronchial tree in MSCT images," Proceedings of SPIE, vol. 6511, Mar. 2007, 10 pages.

Pu, J. et al., "Computerized assessment of pulmonary fissure integrity using high resolution CT," Medical Physics, vol. 37, No. 9, Sep. 2010, pp. 4661-4672.

Pu, J. et al., "Pulmonary Lobe Segmentation in CT Examinations Using Implicit Surface Fitting," IEEE Transactions on Medical Imaging, vol. 28, No. 12, Dec. 2009, pp. 1986-1996, Abstract and author manuscript provided.

Reymond et al., Prediction of Lobar Collateral Ventilation in 25 Patients with Severe Emphysema by Fissure Analysis with CT, AJR—American Journal of Roentgenology (2013), vol. 201, No. 4, pp. W571-W575, AARS, Virginia.

Riquet, M. et al., "Lung cancer invading the fissure to the adjacent lobe: more a question of spreading mode than a staging problem," European Journal of Cardio-Thoracic Surgery, vol. 41, 2012, pp. 1047-1051.

Rodarte, J.R. et al., "Regional lung strain in dogs during deflation from total lung capacity," Journal of Applied Physiology, vol. 85, 1985, pp. 164-172.

Saroul et al., "Exploring curved anatomic structures with surface sections," IEEE Visualization 2003, Annual IEEE Conference on Visualization, New York, NY, Oct. 19, 2003, pp. 27-34.

Saroul, "Surface Extraction and Flattening for Anatomical Visualization," Thesis No. 3575, University of Saint-Etienne, France, 2006, 135 pages.

Sciurba et al., "A Randomized Study of Endobronchial Valves for Advanced Emphysema," The New England Journal of Medicine, vol. 363, No. 13, Sep. 23, 2010, pp. 1233-1244.

Sterman, D.H. et al., "A multicenter Pilot Study of a Bronchial Valve for the Treatment of Severe Emphysema," Respiration, vol. 79, No. 3, 2010, pp. 222-233.

Strange, C. et al., "Design of the Endobronchial Valve for Emphysema Palliation Trial (VENT): a non-surgical method of lung volume reduction," BMC Pulmonary Medicine, vol. 7, Jul. 3, 2007, 12 pages.

The National Lung Screening Trial Research Team, "Reduced Lung-Cancer Mortality with Low-Dose Computed Tomographic Screening," The New England Journal of Medicine, vol. 365, No. 5, Aug. 4, 2011, pp. 395-409.

Ukil, S. et al., "Anatomy-Guided Lung Lobe Segmentation in X-Ray CT Images," IEEE Transactions on Medical Imaging, vol. 28, No. 2, Feb. 2009 pp. 202-214, Abstract only.

Van Rikxoort, E.M. et al., "Automatic Segmentation of Pulmonary Segments From Volumetric Chest CT Scans," IEEE Transactions on Medical Imaging, vol. 28, No. 4, Apr. 2009, pp. 621-630, Abstract only.

Van Rikxoort, E. et al., "A method for the automatic quantification of the completeness of pulmonary fissures: evaluation in a database of subjects with severe emphysema," European Radiology, vol. 22, 2012, pp. 302-309.

Venuta et al., "Long-term follow-up after bronchoscopic lung volume reduction in patients with emphysema," European Respiratory Journal, vol. 39, No. 5, 2012, pp. 1084-1089.

Washko G.R. et al., "Physiological and Computed Tomographic Predictors of Outcome from Lung Volume Reduction Surgery," American Journal of Respiratory and Critical Care Medicine, vol. 181, No. 5, 2010, pp. 494-5000.

Wiemker et al., "Unsupervised Extraction of the Pulmonary Interlobar Fissures from High Resolution Thoracic CT Data," International Congress Series 1281, 2005, pp. 1121-1126.

Witten et al., "Data Mining: Practical Machine Learning Tools and Techniques," Morgan Kaufmann Publishers, Burlington, MA, 2011, Third Edition.

Yee et al., "Animated exploration of dynamic graphs with radial layout", INFOVIS 2001 IEEE Symposium on Information Visualization, Jan. 1, 2001, pp. 43-50.

Yu et al., "System for the analysis and visualization of large 3D anatomical trees", Computers in Biology and Medicine, vol. 37, No. 12, Oct. 17, 2007, pp. 1802-1820.

Yuan et al., "Quantification of lung surface area using computed tomography," Respiratory Research, vol. 11, No. 153, 2010, 9 pages.

Zach et al., "Correlations of CT Low Attenuation Cluster Size with Visually Assessed Extent and Pattern of Emphysema," ATS, 2013, 1 page.

Zhou, X. et al., "Automatic recognition of lung lobes and fissures from multi-slice CT images, " Proceedings of SPIE Medical Imaging, vol. 5370, 2004, pp. 1629-1633.

Valipour et al., "Patterns of Emphysema Heterogeneity," Respiration, Oct. 3, 2015, 10 pages.

* cited by examiner

710

720

730

810

820

830

835

840

845

1110

1120

1130

VISUALIZATION OF SUB-PLEURAL REGIONS

CROSS-REFERENCE TO RELATED APPLICATION

This application claims the benefit of U.S. Provisional Application No. 63/118,808, filed Nov. 27, 2020, the content of which is hereby incorporated by reference in its entirety.

FIELD OF INVENTION

The present invention generally relates to systems and methods to generate richly informative displays of the lungs and other complex anatomical structures.

BACKGROUND

Many systems and methods for visualizing the lungs or other anatomical structures rely on providing a visualization with respect to a 2-dimensional plane, such as one of the images created by a CT scan or by a planar cross-sectional view of 3D model of a patient's lungs. Such visualizations may comprise a cross-sectional display image such as those known in the art. However, the nature and extent of some diseases are not ideally observed on standard 2D views. In some instances, planar cross-sectional images may not provide an optimal context in which to view various conditions and/or diseases. A physician may be forced to observe a sub-optimal view or look at multiple cross-sectional images at a time which can result in confusion and mis-identification of diseases. Accordingly, systems and methods for better visualizing regions of the lungs may be useful in observing various lung characteristics, such as the presence and/or extent of lung diseases.

SUMMARY

In one aspect of the present disclosure, a method for visualizing sub-pleural regions of an anatomical structure of interest from a set of volumetric data can include receiving the set of volumetric data representative of the anatomical structure of interest. The anatomical structure of interest can comprise an outer surface and a plurality of sub-pleural regions. Each of the plurality of sub-pleural regions can be a region of the anatomical structure of interest which is distant from the outer surface by a corresponding sub-pleural depth. The method can also include determining a first sub-pleural region of the anatomical structure of interest. The method can further include extracting, from the set of volumetric data, the portions of volumetric data representative of the first sub-pleural region and extracting, from the set of volumetric data, the portions of volumetric data representative of the first sub-pleural region.

In another aspect of the present disclosure, a non-transitory computer readable medium is programmed with instructions to cause one or more processors to receive a set of volumetric data representative of an anatomical structure of interest. The anatomical structure of interest can include an outer surface and a plurality of sub-pleural regions, each of the plurality of sub-pleural regions being a region of the anatomical structure of interest which is distant from the outer surface by a corresponding sub-pleural depth. The non-transitory computer readable medium can also be programmed with instructions to cause the one or more processors to determine a first sub-pleural region of the anatomical structure of interest, extract, from the set of volumetric data, the portions of volumetric data representative of the first sub-pleural region, and to render a display image based upon the first sub-pleural region and the extracted volumetric data.

In another aspect of the present disclosure, a system includes a memory with the memory configured to store volumetric data. The system can also include a processor configured to receive a set of volumetric data representative of an anatomical structure of interest. The anatomical structure of interest can include an outer surface and a plurality of sub-pleural regions with each of the plurality of sub-pleural regions being a region of the anatomical structure of interest, which is distant from the outer surface by a corresponding sub-pleural depth. The processor can further be configured to determine a first sub-pleural region of the anatomical structure of interest and extract, from the set of volumetric data, the portions of volumetric data representative of the first sub-pleural region. The processor can additionally be configured to render a display image based upon the first sub-pleural region and the extracted volumetric data.

DETAILED DESCRIPTION

Figure 1:
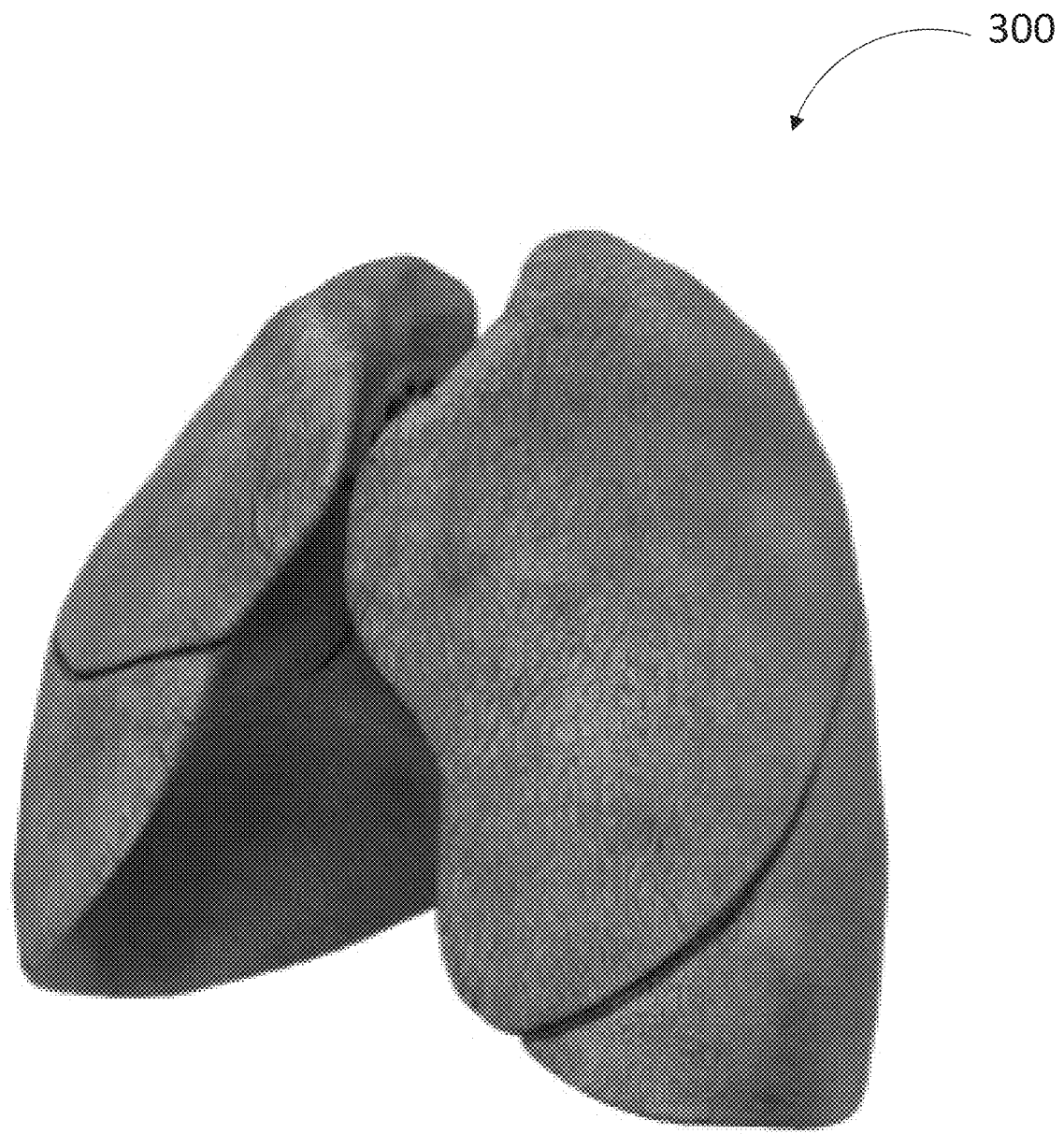
FIG. 1 illustrates an example three-dimensional model of a pair of lungs according to an aspect of the present disclosure.

Aspects of this disclosure generally relate to systems and methods for producing displays of anatomical structures from medical image data. Medical image data may be patient images or imaging data produced by CT scans, MRI scans, PET scans and/or other volumetric images, for example. Therefore, while this application may refer to CT generally, or to quantitative CT measurements, it should be understood that other imaging modalities may also be used, and embodiments of the invention are not limited to CT based measurements.

This disclosure includes methods to provide visualization of anatomical features in two and three dimensions. In general, various embodiments relating to systems and methods to generate richly informative displays of lungs and other complex anatomical structures are disclosed herein. Such embodiments can be used in an exemplary application to allow a physician or other user to visualize a patient's lungs or the like.

Interstitial lung disease (ILD) often manifests in the lung periphery such as just beneath the lung pleurae (e.g. the outer 'skin' or outer surface of the lungs) in a sub-pleural region. Observing ILD with conventional cross-sectional images, as described herein, may result in the mis-identification of disease severity, progression, or the like. Accordingly, systems and methods for visualizing sub-pleural regions of the lungs may be useful in observing various lung characteristics, such as the presence of ILD.

The outer surface 110 of the lung may already be identified within data representative of such outer surfaces 110 or such outer surfaces 110 may be identified within volumetric image data representative of a patient's lungs. Such data may comprise data denoting which voxels or pixels represent the outer surface 110.

Additionally or alternatively, the outer surface 110 of the lung may be determined via image analysis. In some embodiments, the outer surface of the lung can be segmented using the 2D or 3D image data. The methods of performing segmentation from the volumetric images or imaging data may be similar to or the same as those employed by the Pulmonary Workstation of Vida Diagnostics, Inc. (Coralville, Iowa) and as described in the following references, each of which is incorporated herein by reference: United States Patent Publication 2007/0092864, which is entitled: Treatment Planning Methods, Devices and Systems; United States Patent Publication 2006/0030958, which is entitled: Methods and Devices for Labeling and/or Matching; Tschirren et al., "Intrathoracic airway trees: segmentation and airway morphology analysis from low-dose CT scans," IEEE Trans Med Imaging. 2005 Dec. 24 (12):1529-39; Tschirren et al., "Matching and anatomical labeling of human airway tree," IEEE Trans Med Imaging. 2005 Dec. 24 (12):1540-7; Tschirren, Juerg, "Segmentation, Anatomical Labeling, Branchpoint Matching, and Quantitative Analysis of Human Airway Trees in Volumetric CT Images," Ph.D. Thesis, The University of Iowa, 2003; Tschirren, Juerg, Segmentation, Anatomical Labeling, Branchpoint Matching, and Quantitative Analysis of Human Airway Trees in Volumetric CT Images, Slides from Ph.D. defense, The University of Iowa, 2003; and Li, Kang, "Efficient Optimal Net Surface Detection for Image Segmentation—From Theory to Practice," M.Sc. Thesis, The University of Iowa, 2003, for example. Segmentation of the lungs, the outer surface of the lungs, and/or sub-pleural regions can result in the identification of the lungs, the outer surface of the lungs, and/or sub-pleural regions as distinct from other surrounding features (e.g. surrounding tissues, bones). In some embodiments, a segmentation process or the like may be used to determine the outer surface 110 and/or various other features present in the volumetric data. Determining the outer surface 110 may comprise a process similar to that described in U.S. Patent Publication 2014/0105472 with respect to identifying and extracting various features of the lungs. Furthermore, a "lung mask" or the like may be applied to images to remove excess or irrelevant features, such as the chest wall around the lungs, as described in U.S. Patent Publication 2015/0332454.

The step of determining the outer surface 110 may be carried out by a system and/or via a non-transitory computer-readable medium. Systems may include a processor, such as a processor in an electronic device (e.g. computer, smart phone, tablet, etc.), and may also include a visual display such as a monitor or other display screen to present visual displays to a user such as a physician as discussed herein. The system may also include instructions included in software, stored in a memory of the system, and operable on the processor. The software may include instructions for the processor to perform the various steps and methods described herein, including instructions to receive volumetric image data, determine the outer surface 110, project a sub-pleural region, and/or the like. The software may further include instructions to display images including three-dimensional images and/or two-dimensional images of anatomical structures such as the lungs, sub-pleural regions, or the like. The software for analyzing volumetric images, as described herein, may include 3D imaging software such as LungPrint quantitative pulmonary imaging software, from VIDA Diagnostics, Inc., or the like.

FIG. 1 provides an example of a three-dimensional model of a pair of lungs 300. In some embodiments, a 3-D representation of an anatomical structure, such as lungs 300, may be provided and/or constructed previously. Additionally or alternatively systems and methods may be used to construct the three-dimensional anatomical structure. For example, volumetric image data may comprise a plurality of two-dimensional images, such as those shown in FIG. 2. Such images may be stacked or layered to then represent a three-dimensional model, such as shown in FIG. 1. In either the visualizations shown in FIG. 1 or FIG. 2, the outer surface of the lungs may be identified manually or via a system and/or via a non-transitory computer-readable medium.

Figure 3:
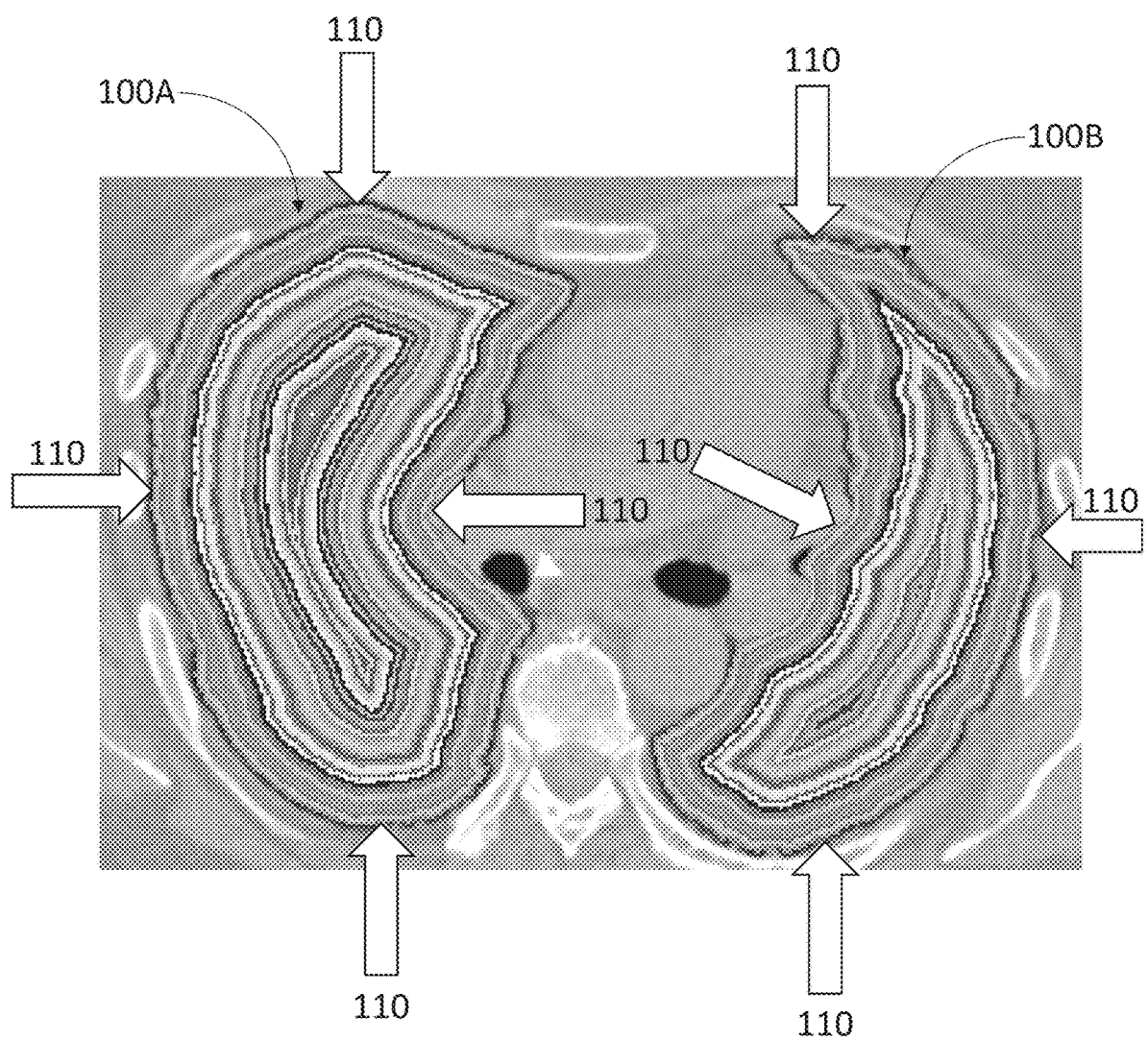
FIG. 3 illustrates an example schematic axial cross-sectional view of a pair of lungs including sub-pleural regions according to an aspect of the present disclosure.

FIG. 3 provides a schematic axial cross-sectional view of a pair of lungs 100A, 100B. The outer surface 110 of the lungs 100A, 100B (e.g. the lung pleurae, the visceral pleura) are indicated by the series of arrows. Sub-pleural regions inside lungs 100A and 100B are shown schematically as adjacent layers interior to the outer surface 110. As discussed herein, it may be beneficial to image all or a portion of sub-pleural regions to analyze the lungs for various purposes.

Figure 4:
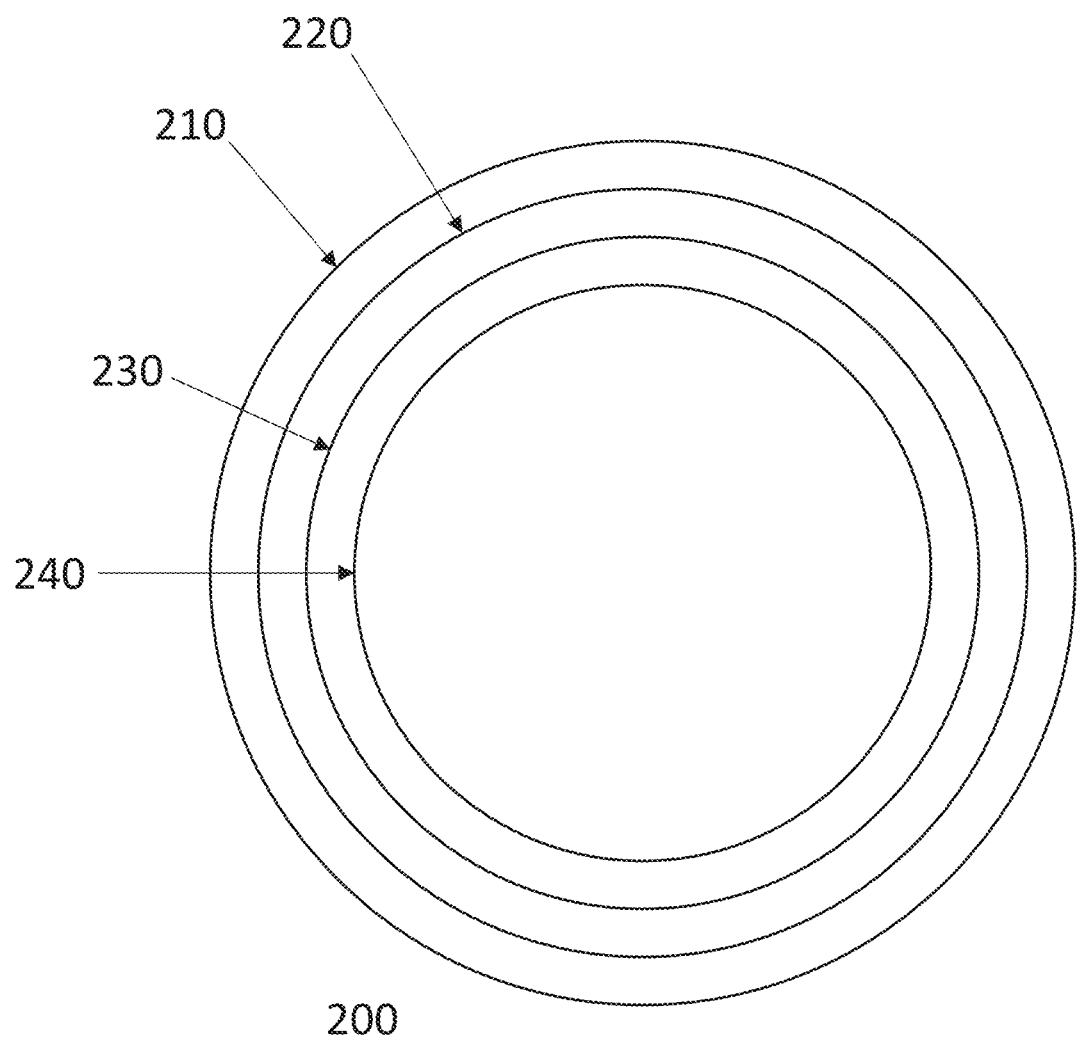
FIG. 4 illustrates an example cross-sectional view of an anatomical structure that includes various sub-pleural regions according to an aspect of the present disclosure.

FIG. 4 illustrates a simplified cross-section of an anatomical structure 200 (e.g. the lungs) along with various sub-pleural regions of anatomical structure 200. As shown in FIG. 4, each sub-pleural region may be a region of a particular depth relative to the outer surface 210. As described herein, the outer surface 210 may be representative of the lung pleurae and then regions 220-240 may be representative of various sub-pleural regions at different depths. The depth may be defined as normal to the outer surface of the anatomical structure. For example, sub-pleural region 220 may represent a depth of 2 mm (e.g. 2 mm offset from the outer surface of anatomical structure 200), sub-pleural region 230 may represent a depth of 4 mm, and sub-pleural region 240 may represent a depth of 6 mm. As described with respect to sub-pleural regions 220-240, the resolution (e.g. adjustments between depths of sub-pleural regions may be 2 mm). However, various other resolutions may be used.

A plurality of points (e.g. voxels or pixels) comprised on the outer surface of the anatomical structure may be used when determining a sub-pleural region. In some examples, the outer surface of the anatomical structure (e.g. the lungs) may be determined or provided prior to rendering the 3-D representation. Additionally or alternatively, the outer surface may be determined after rendering the 3-D representation. The plurality of points may be used when determining a sub-pleural region of a particular depth. For example, the direction normal to the outer surface at each of a first plurality of points may be determined, and then a secondary set of points may be found representative of the first plurality of points being offset by the particular depth into the anatomical structure in the corresponding normal direction for each of the first plurality of points. Accordingly, the corresponding sub-pleural region may comprise the second plurality of points, a surface or layer representative of the second plurality of points, or the like.

Figure 5A:
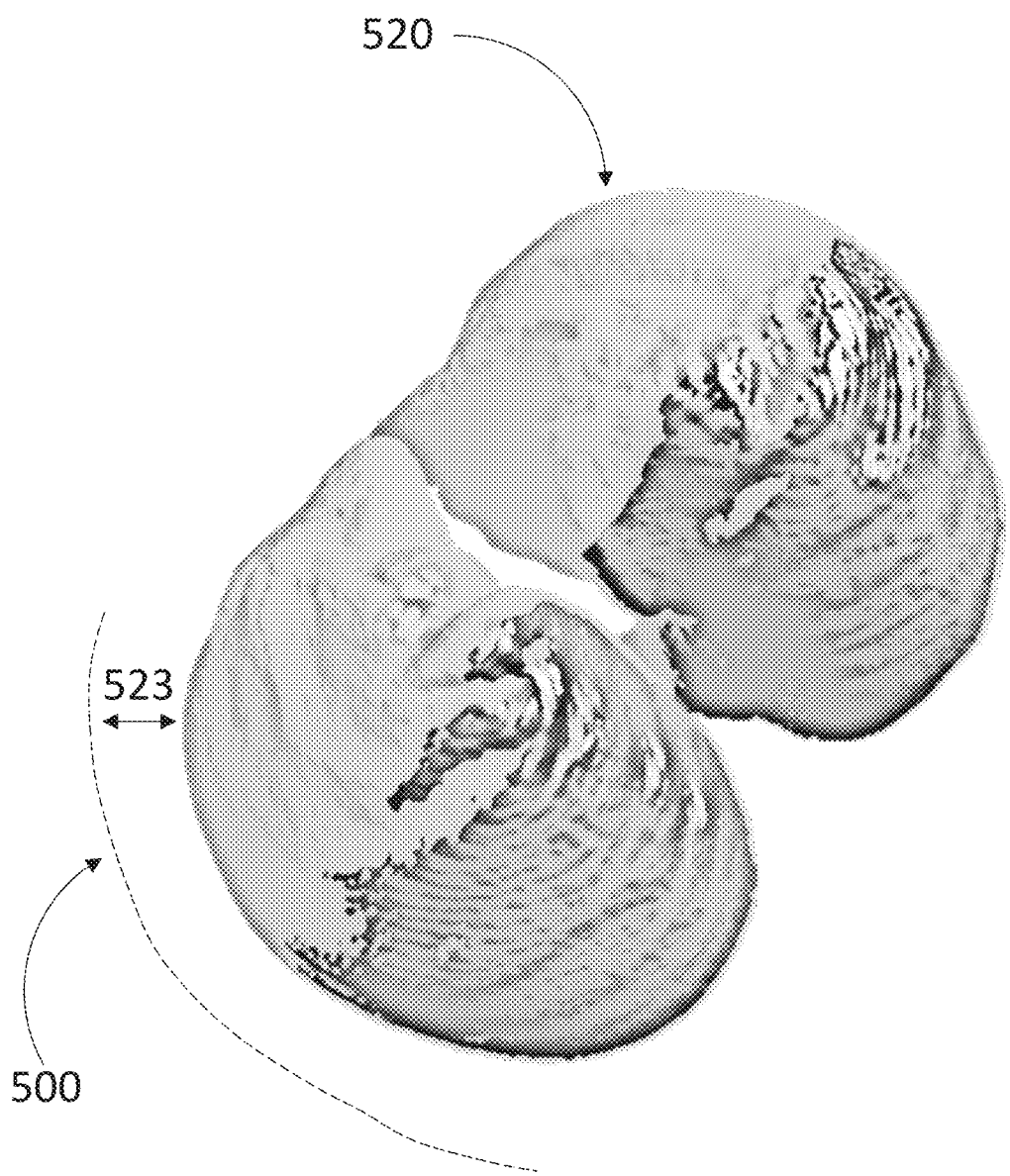
FIG. 5A illustrates an example three-dimensional illustration of a sub-pleural region of an anatomical structure according to an aspect of the present disclosure.

FIG. 5A provides an exemplary 3D illustration of a sub-pleural region 520, such as a sub-pleural region determined using methods as described herein. As shown, sub-pleural region 520 may be the region which is a depth 523 from the outer surface 500 of the anatomical structure. In some embodiments, multiple sub-pleural regions, such as multiple sub-pleural regions of different depths, may be used. Various sub-pleural regions of different depths may provide indications regarding the health or disease state of the overall anatomical structure (e.g. the lungs). For instance, some diseases may initiate close to the peripheral edge of the lungs. In such instances, the disease state of the lungs may be determined based on which sub-pleural regions the disease is prevalent in. It may be difficult, however, to observe the sub-pleural region via a 3-D model and/or it may not be preferred.

Figure 5B:
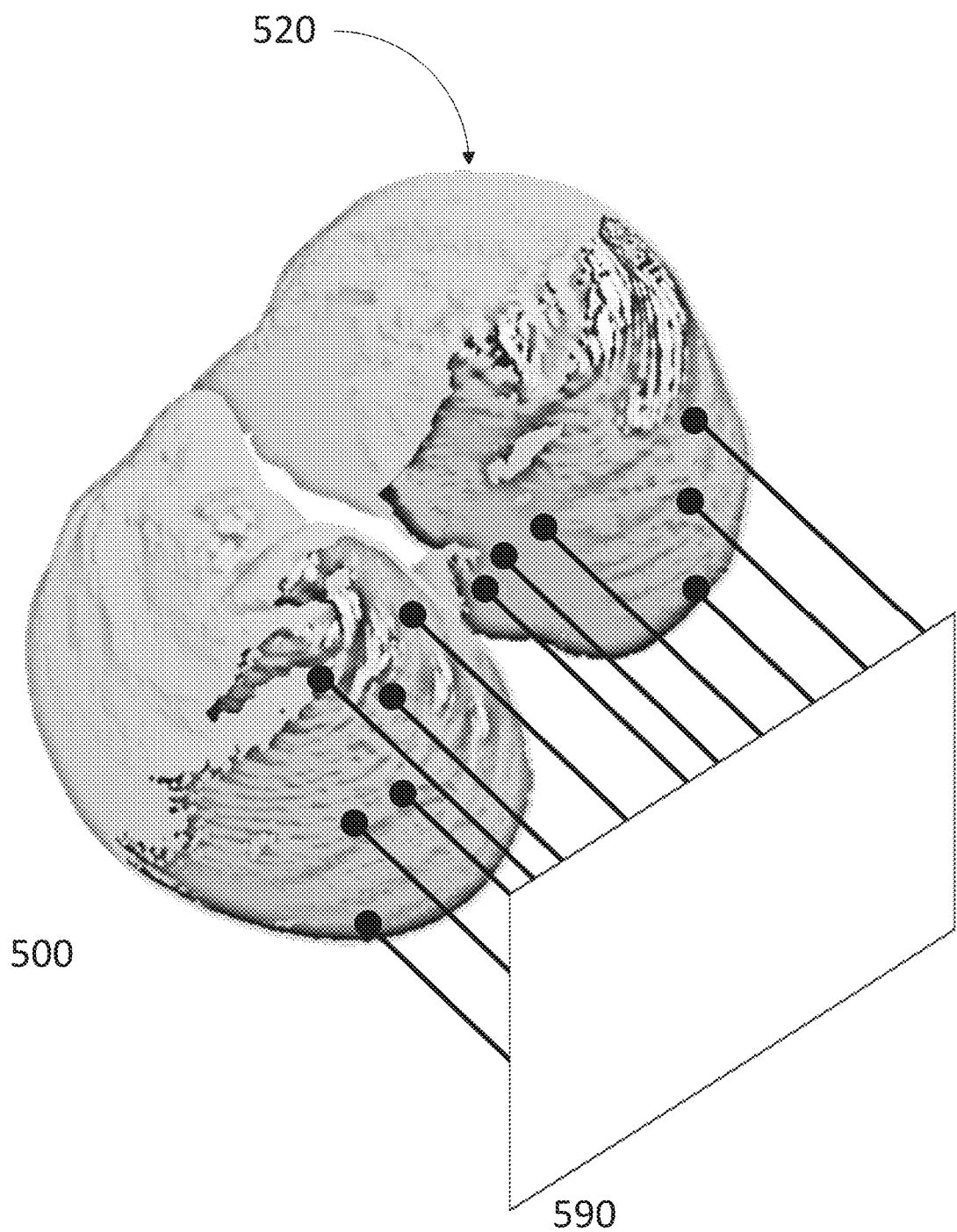
FIG. 5B illustrates an example projection of a sub-pleural region onto a display image according to an aspect of the present disclosure.

In some embodiments, the sub-pleural region (e.g. sub-pleural region 520) may be projected onto a display image, such as shown in FIG. 5B. Projecting the sub-pleural region onto a display image, such as a 2-D display image may provide a better visualization to a user or physician. For example, it may be difficult to observe the sub-pleural region via a 3-D model and/or it may not be preferred. Thus, a sub-pleural region and/or a portion of the sub-pleural region may be projected onto a display image, such as to provide a two-dimensional display image. FIG. 5B provides an exemplary illustration of how a sub-pleural region 520 may be projected onto a display image 590. All or a portion of the sub-pleural region can be projected onto display image 590. In such instances, the selected portion of sub-pleural region 520 to projection onto display image 390 may be the portions directly viewable from the direction of the display image 590. Additionally or alternatively, various other projects may be used to project all or a portion of sub-pleural region 520, such as UV mapping or the like.

Figure 5C:
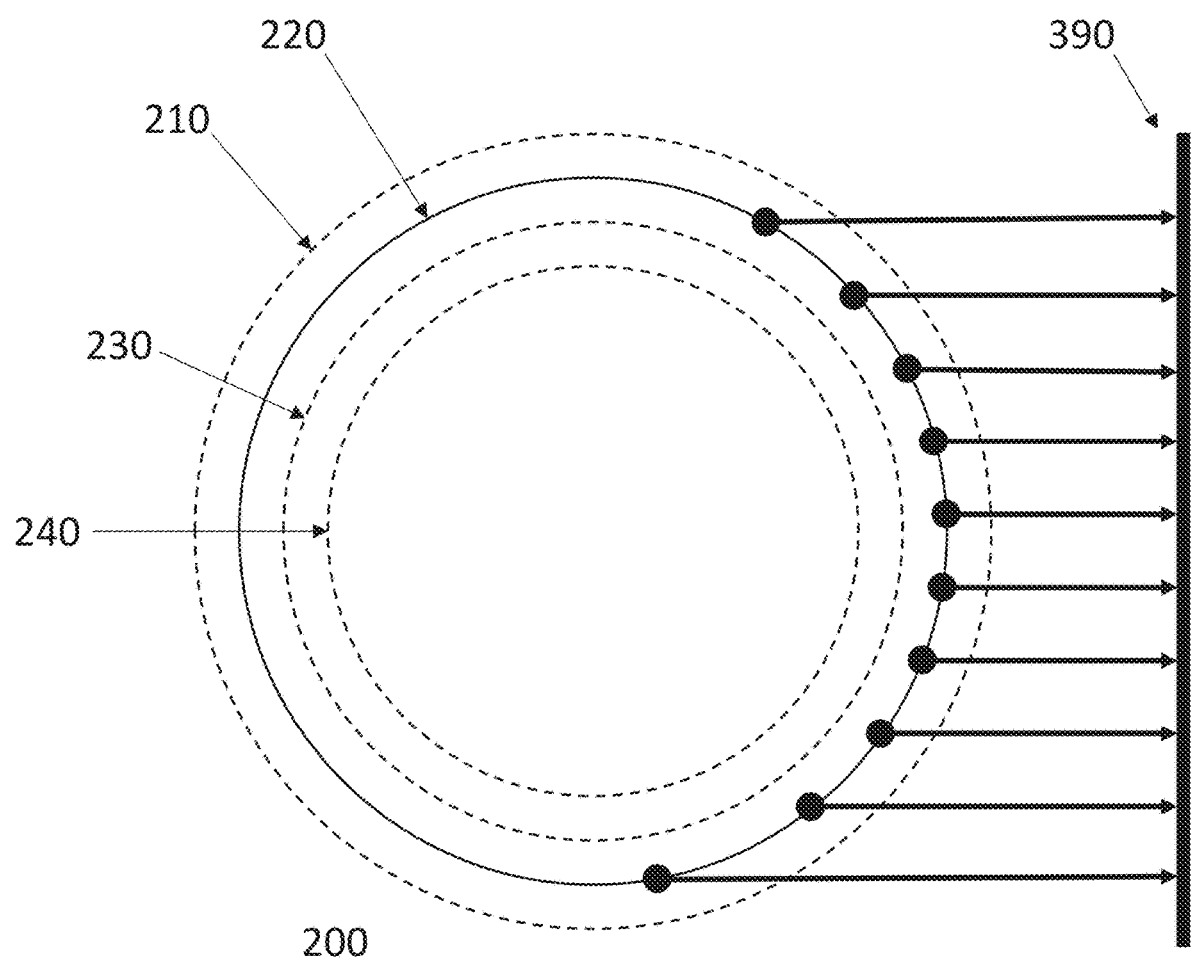
FIG. 5C illustrates an example projection of a sub-pleural region onto a two-dimensional display image according to an aspect of the present disclosure.

FIG. 5C provides a simplified two-dimensional illustration of projecting anatomical structure 200 onto an image plane 390. As shown, a sub-pleural region may be selected or determined (e.g. sub-pleural region 220). Then, that sub-pleural region may be projected onto the image plane 390. In some embodiments, projecting a sub-pleural region (e.g. sub-pleural region 220, 520) may comprise projecting a plurality of points (e.g. voxels, pixels, or the like) comprised on the sub-pleural region. As in FIG. 5B and 5C, a plurality of points may be used when mapping the sub-pleural region onto an image plane/display image. In some embodiments, the plurality of points may comprise all or some of the second plurality of points used to determine the sub-pleural region, as described herein.

Figure 6:
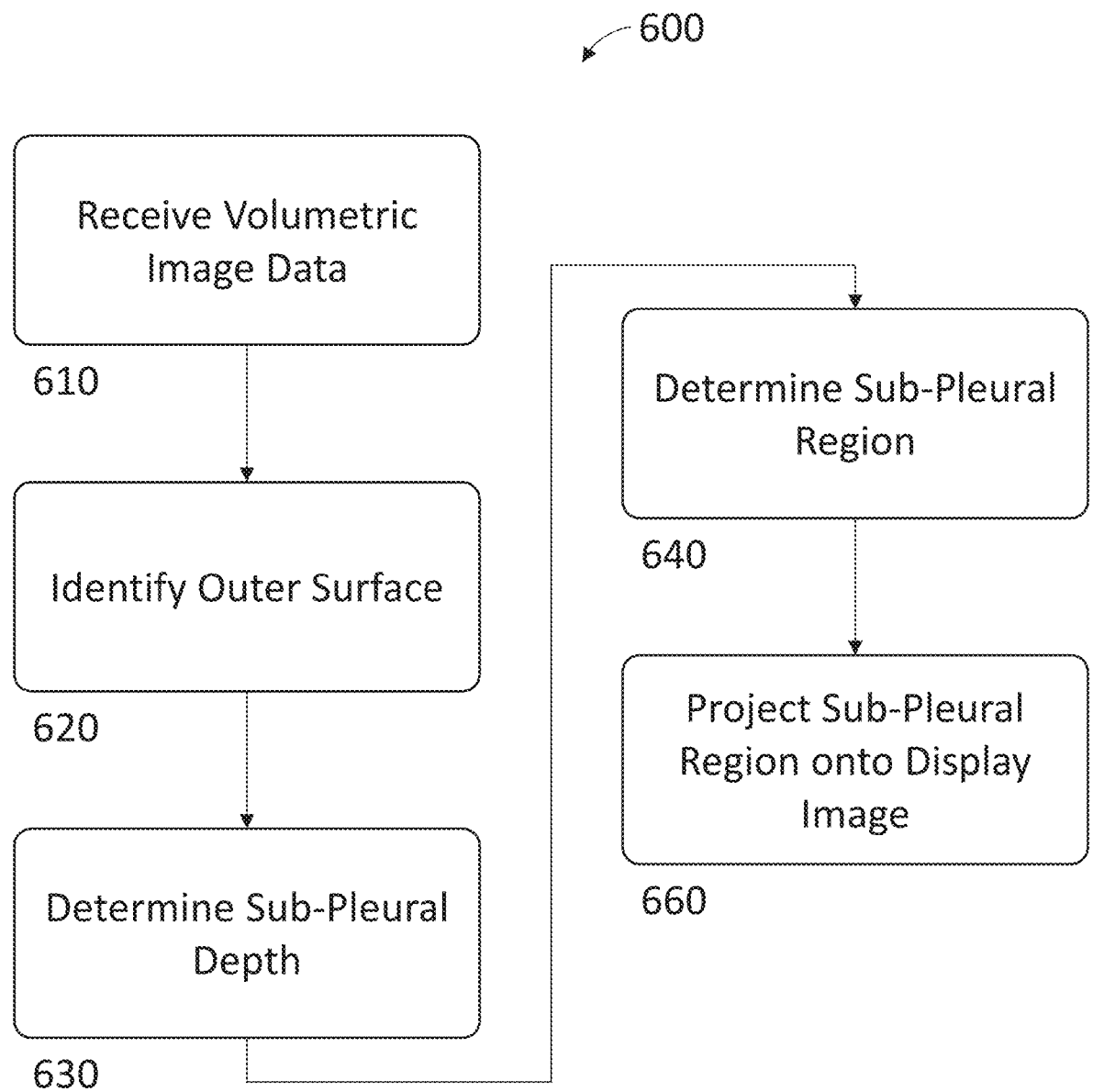
FIG. 6 illustrates an example method for imaging a sub-pleural region of an anatomical structure according to an aspect of the present disclosure.

FIG. 6 provides an exemplary method 600 for imaging a sub-pleural region of an anatomical structure, such as the lungs. As shown, method 600 may comprise receiving volumetric image data (step 610). In some embodiments, the volumetric image data may be representative of only the anatomical structure, representative of the anatomical structure as well as surrounding features, or the like.

Method 600 may additionally comprise the step of identifying an outer surface of the anatomical structure (step 620). As described herein, identifying an outer surface may comprise manual identification from a user or physician. In some instances, the volumetric image data may comprise pre-segmented data, such as to distinguish the anatomical structure from other features present in the image data. Additionally or alternatively, identifying the outer surface may comprise segmenting the volumetric image data such as to identify where the anatomical structure ends and other features begin, or the like.

Method 600 may include the step of determining a sub-pleural depth (step 630). Determining the sub-pleural depth may comprise receiving a selection, such as from a physician or user via a user interface. Step 630 may comprise receiving an input of a particular depth of interest (e.g. 1 mm, 1 inch, 3 cm, etc.). Additionally or alternatively, a user may cycle through a variety of depths, such as by adjusting the depth up and down via a user interface (e.g. with arrow keys, a scroll wheel, gestures on a touch sensitive display, or the like).

Figure 2:
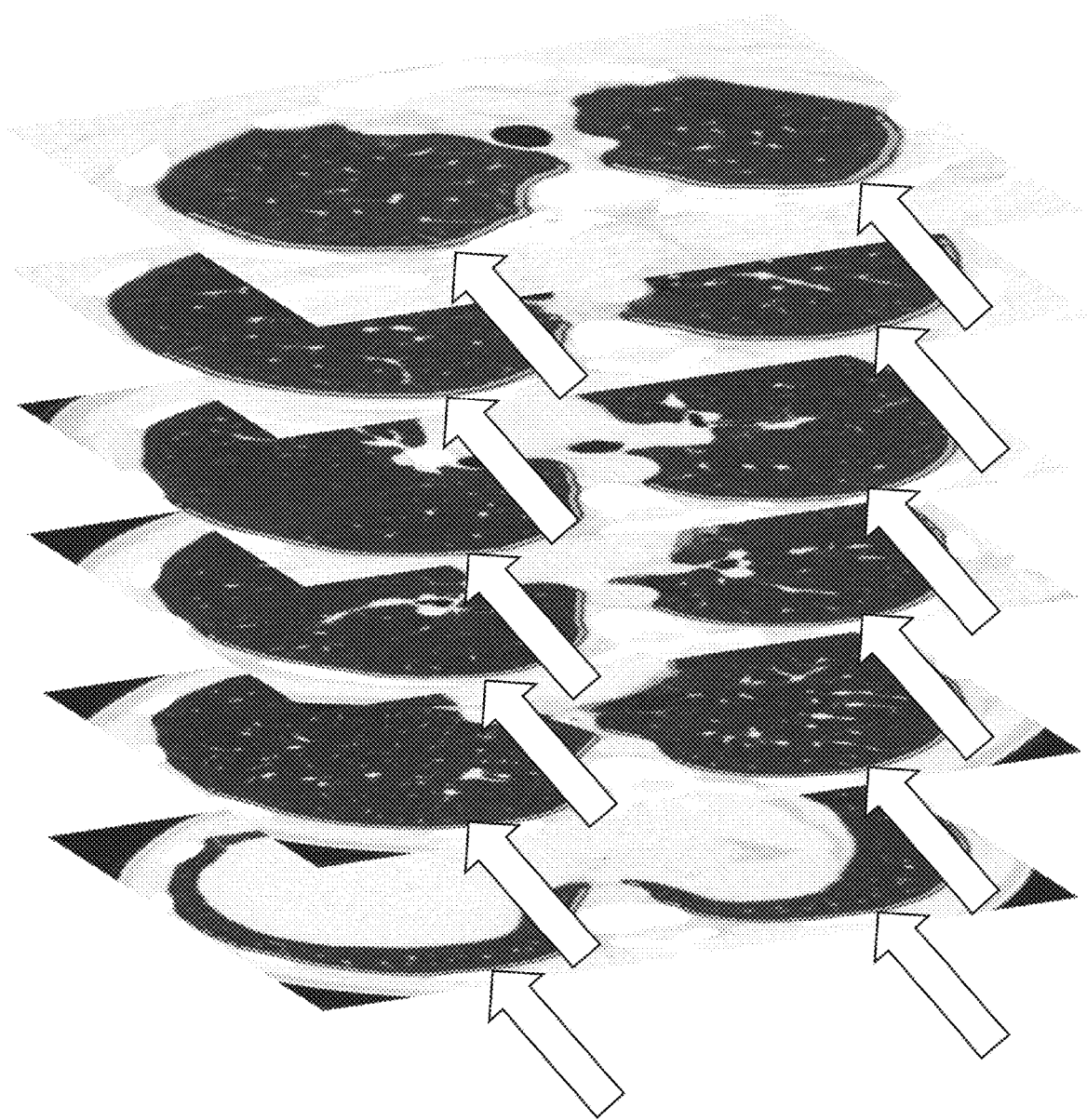
FIG. 2 illustrates an example of multiple two-dimensional images which can be stacked or layered to represent a three-dimensional model of a pair of lungs according to an aspect of the present disclosure.

After determining the sub-pleural depth, method 600 may further comprise determining the associated sub-pleural region (step 640). As discussed herein, the sub-pleural region may be the region of the anatomical structure which is offset in a direction normal to the outer surface by a particular depth. In some embodiments, the volumetric data may comprise a plurality of points, or voxels, comprised on or near the outer surface of the anatomical structure of interest. The direction normal to the outer surface at each voxel can be used to determine the offset direction. In some embodiments, the offset direction can be determined in two dimensional cross-sections, such as shown in FIG. 2 or 3. Additionally or alternatively, the offset direction can be determined in other spatial representations, such as in a three-dimensional model of the anatomical structure of interest or the like.

Method 600 may additionally comprise the steps of projecting the sub-pleural region onto a display image (step 650). In some embodiments, step 650 may comprise determining a portion or all of the sub-pleural region to project onto the display image, such as described herein with respect to FIGS. 3 and 5. Determining the portion of the sub-pleural region to project may comprise receiving a selection from a physician or other user, such as via a user interface. For example, a physician may select one or more viewing directions and/or projection methods.

Figure 7:
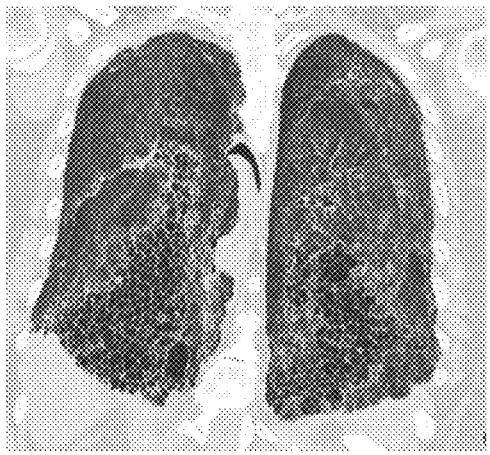
FIG. 7 illustrates an example of sub-pleural display images of lungs according to an aspect of the present disclosure.
Figure 7:
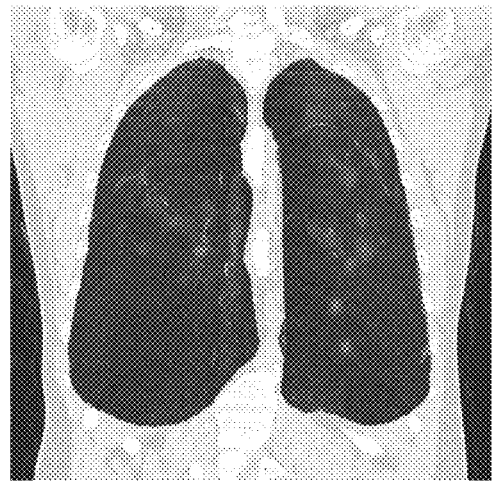
Figure 7:
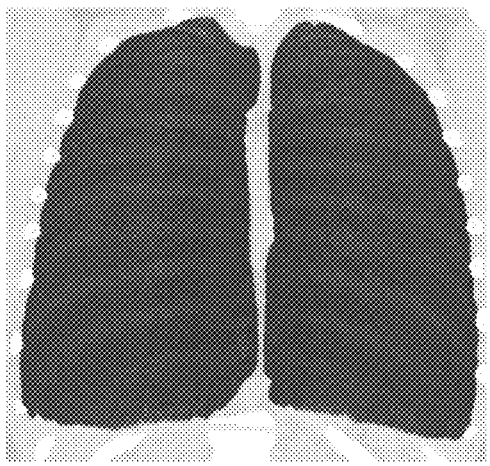

FIG. 7 provide some exemplary sub-pleural display images of lungs. In particular, display image 710 provides an exemplary display image of a pair of lungs with interstitial lung disease, display image 720 provides an exemplary display image of a pair of lungs with COVID-19, and display image 730 provides an image of a pair of lungs with no underlying health conditions. As shown, the sub-pleural regions shown in display images 710 and 720 help illustrate differences between the diseased lungs and the normal lungs of display image 730.

Figure 8A:
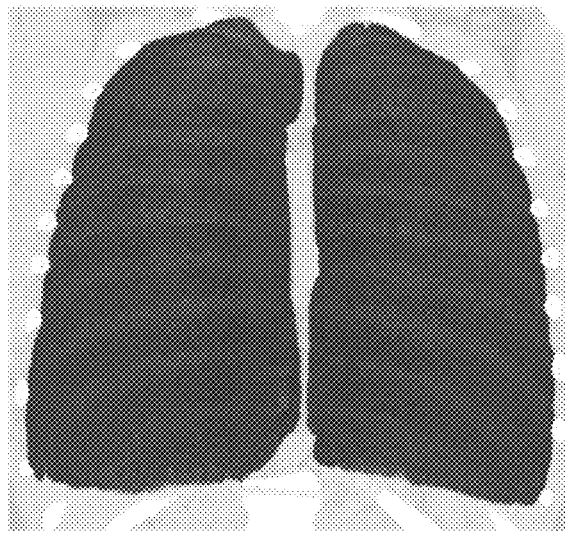
FIG. 8A and FIG. 8B illustrate multiple, example display images of a pair of lungs which are taken from various directions according to an aspect of the present disclosure.
Figure 8A:
Figure 8A:
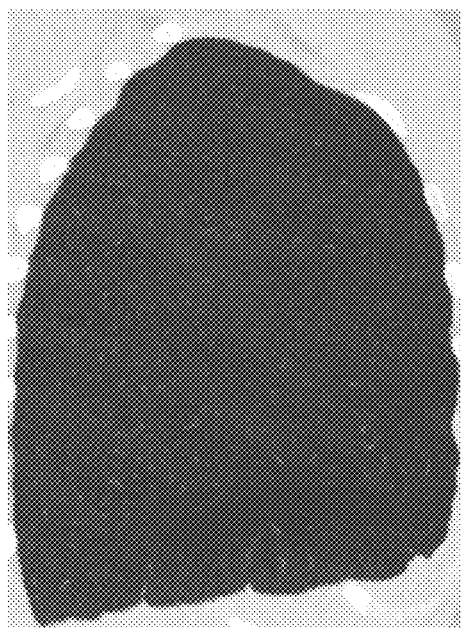
Figure 8B:
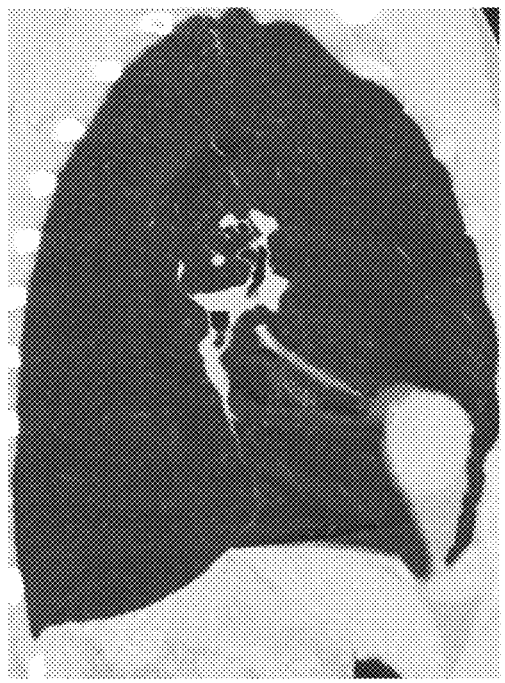
Figure 8B:
Figure 8B:

In some embodiments, it may be advantageous to provide multiple display images of an anatomical structure. For example, a physician may be provided with a plurality of display images of an anatomical structure, each having different perspectives, a plurality of depths, and/or be taken at a plurality of times. Using multiple display images may provide the physician with additional details, such as to better analyze the anatomical structure, determine the presence of any diseases, abnormalities, or the like. As described herein, multiple display images may be captured at a determined sub-pleural depth. FIG. 8A-FIG. 8B provide an exemplary illustration of multiple display images used to visualize a pair of lungs from multiple directions. As shown, display image 810 provides a view of the posterior of the lungs (e.g. a right lung and a left lung) and display image 820 provides a view of the anterior of the lungs. Furthermore, display image 830 provides a view of an exterior portion of the right lung and display image 835 provides a view of an interior portion of the right lung. Similarly, display image 845 provides a view of an exterior portion of the left lung and display image 840 provides a view of an interior portion of the left lung.

With respect to FIG. 8A-FIG. 8B, the multiple display images may be provided based on predetermined viewing directions, such as standard viewing directions in a particular field. For example, physicians may standardly view an anatomical structure such as the lungs from the front, back, left and right. Accordingly, a physician may be presented with such standard views. In some embodiments, the physician may be presented with the standard views automatically, or the views may be selectable (e.g. such as via a user interface).

Figure 9A:
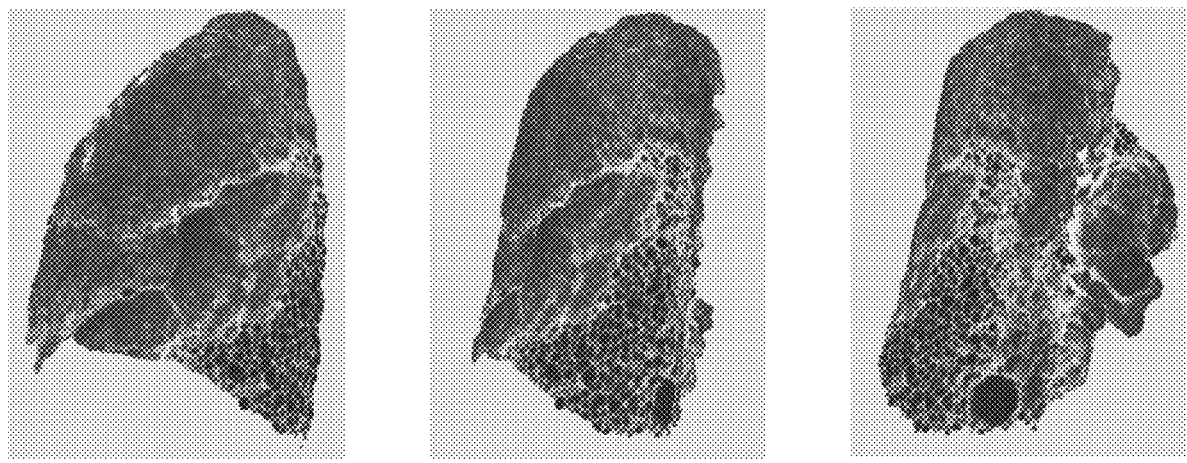
FIG. 9A-FIG. 9C illustrate multiple, example display images of a pair of lungs which are taken over a 360-degree rotation according to an aspect of the present disclosure.
Figure 9B:
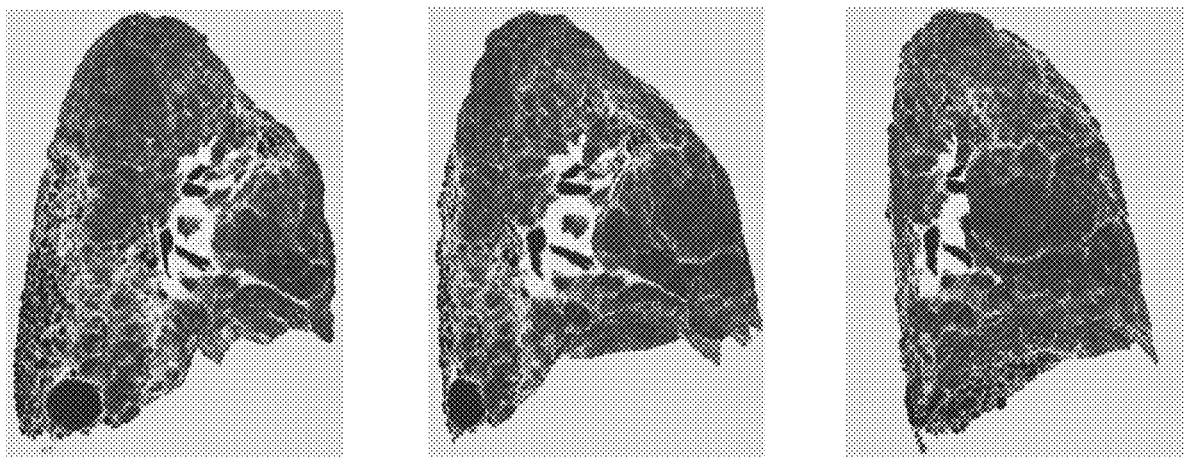
Figure 9C:
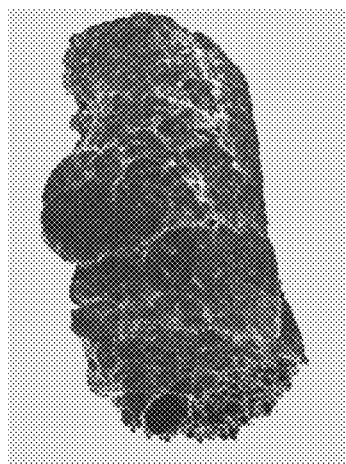
Figure 9C:
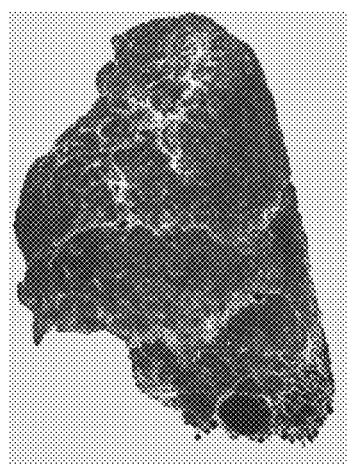
Figure 9C:
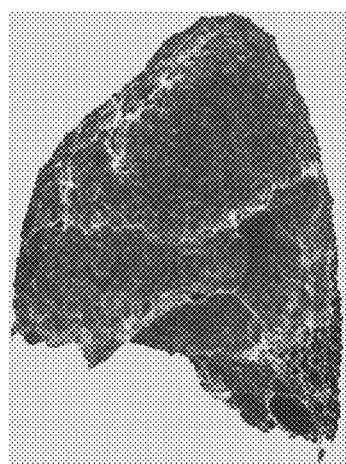

Additionally or alternatively, systems and methods may further include determining a number of images to be captured for a particular amount of rotation. FIG. 9A-FIG. 9C provide an example of nine images captured over a 360-degree rotation. In some embodiments, display images may be captured uniformly over the rotation (e.g. 0 degrees, 40 degrees, 80 degrees, 120 degrees, etc.). Additionally or alternatively, the perspective may not be evenly distributed. For example, the perspectives may be manually selected by a user, come from a preset selection, or the like. Furthermore, the perspectives do not need to be limited to perspectives from a single axis of rotation. Any perspective from around the anatomical structure of interest, or the like has been contemplated.

Figure 10A:
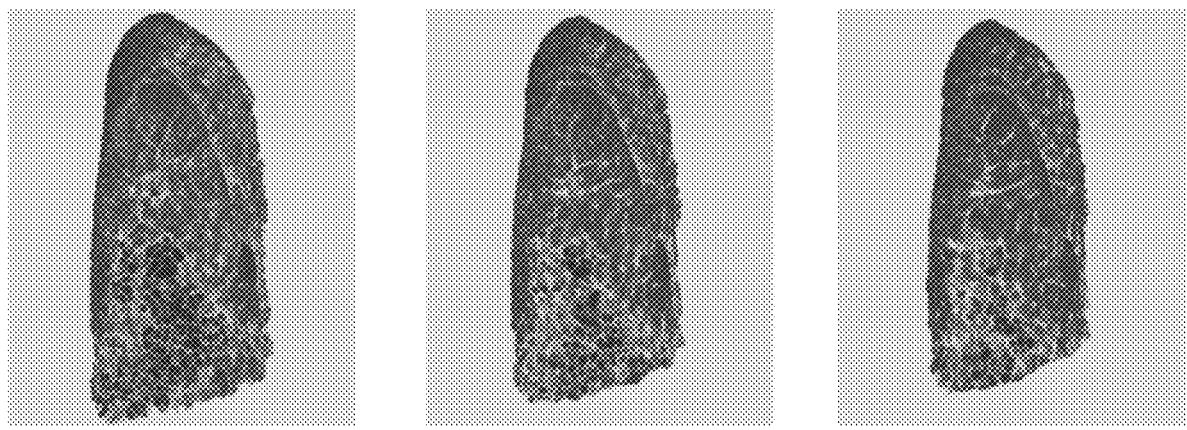
FIG. 10A-FIG. 10C illustrate multiple, example display images of a pair of lungs which are captured at progressively deeper sub-pleural depths according to an aspect of the present disclosure.
Figure 10B:
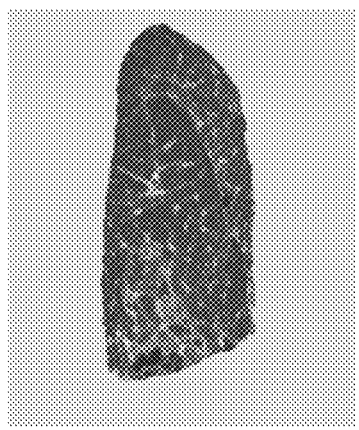
Figure 10B:
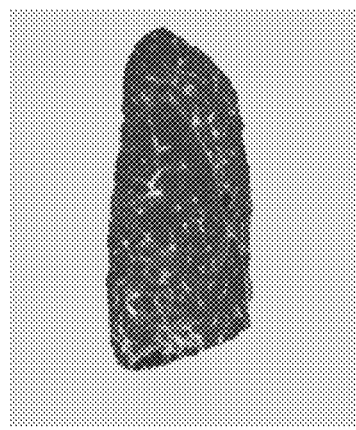
Figure 10B:
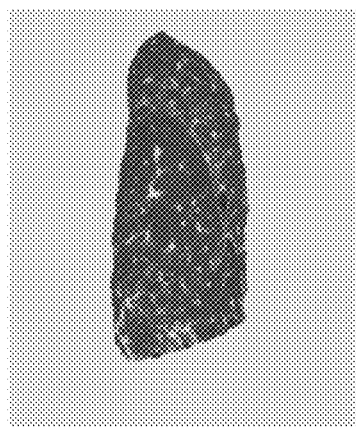
Figure 10C:
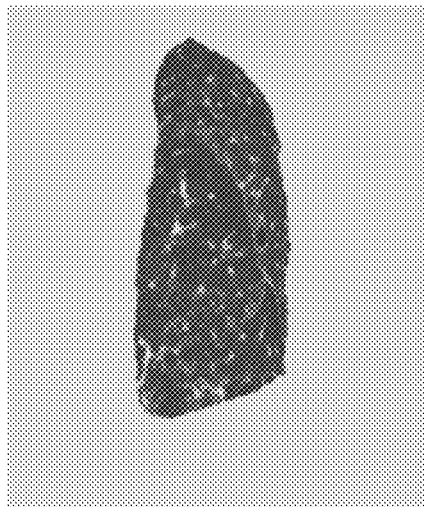
Figure 10C:
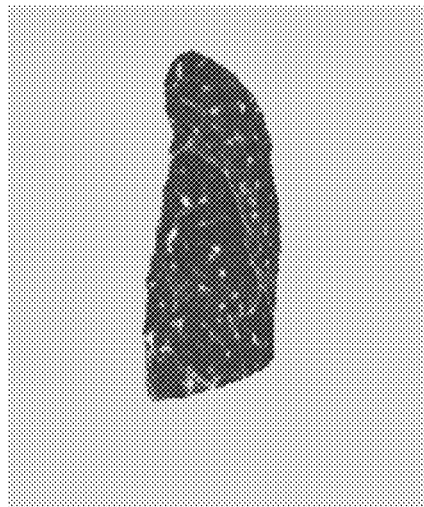

Capturing multiple display images may also comprise capturing multiple display images at a variety of sub-pleural depths. FIG. 10A-FIG. 10C provide an exemplary embodiment wherein 8 display images are captured at progressively deeper sub-pleural depths. In some embodiments, a certain amount of display images may be uniformly captured from a first depth to a second depth. For instance, ten display images may be captured every 3 mm for 30 mm of depth. Additionally or alternatively, the plurality display images may comprise depths of interest and the depths need not be uniformly distributed. For example, the depths may be manually selected by a user, come from a preset selection, or the like.

Figure 11:
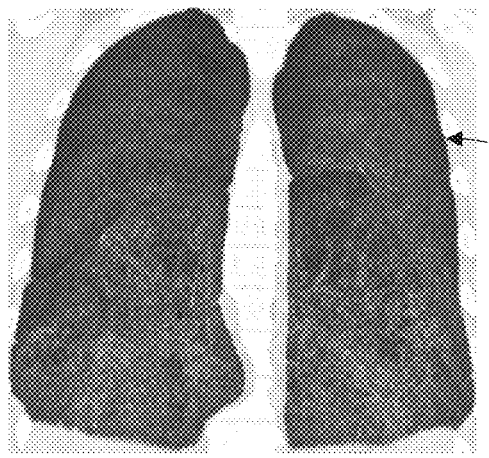
FIG. 11 illustrates an example of selected sub-pleural regions of a patient's lungs being imaged over time according to an aspect of the present disclosure.
Figure 11:
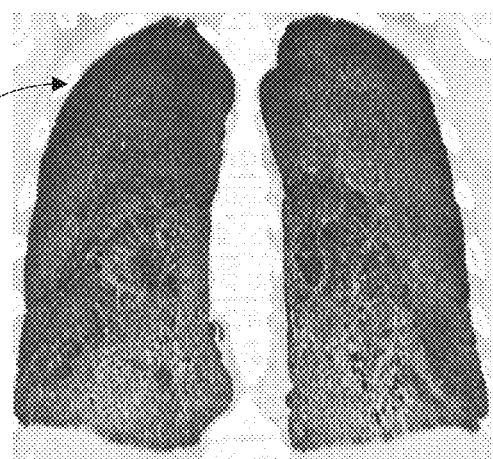
Figure 11:

In some instances, it may be beneficial to capture multiple display images over a period of time. In some embodiments, the period of time may be shorter, such as during a single visit to a physician. Additionally or alternatively, the period of time may comprise longer gap, such as monthly, yearly, during every physician visit, or the like. FIG. 11 provides an exemplary embodiment of a selected sub-pleural region 1100 of a patient's lungs being imaged over time. As shown, display image 1110 may be from a first time, display image 1120 may be from a second time after the first time, and display image 1130 may be from a third time after the second time. As can be seen via the changes between display images 1110-1130, sub-pleural regions may slowly change overtime, indicating the progression of a disease, the regression of a disease, or the like.

Figure 12:
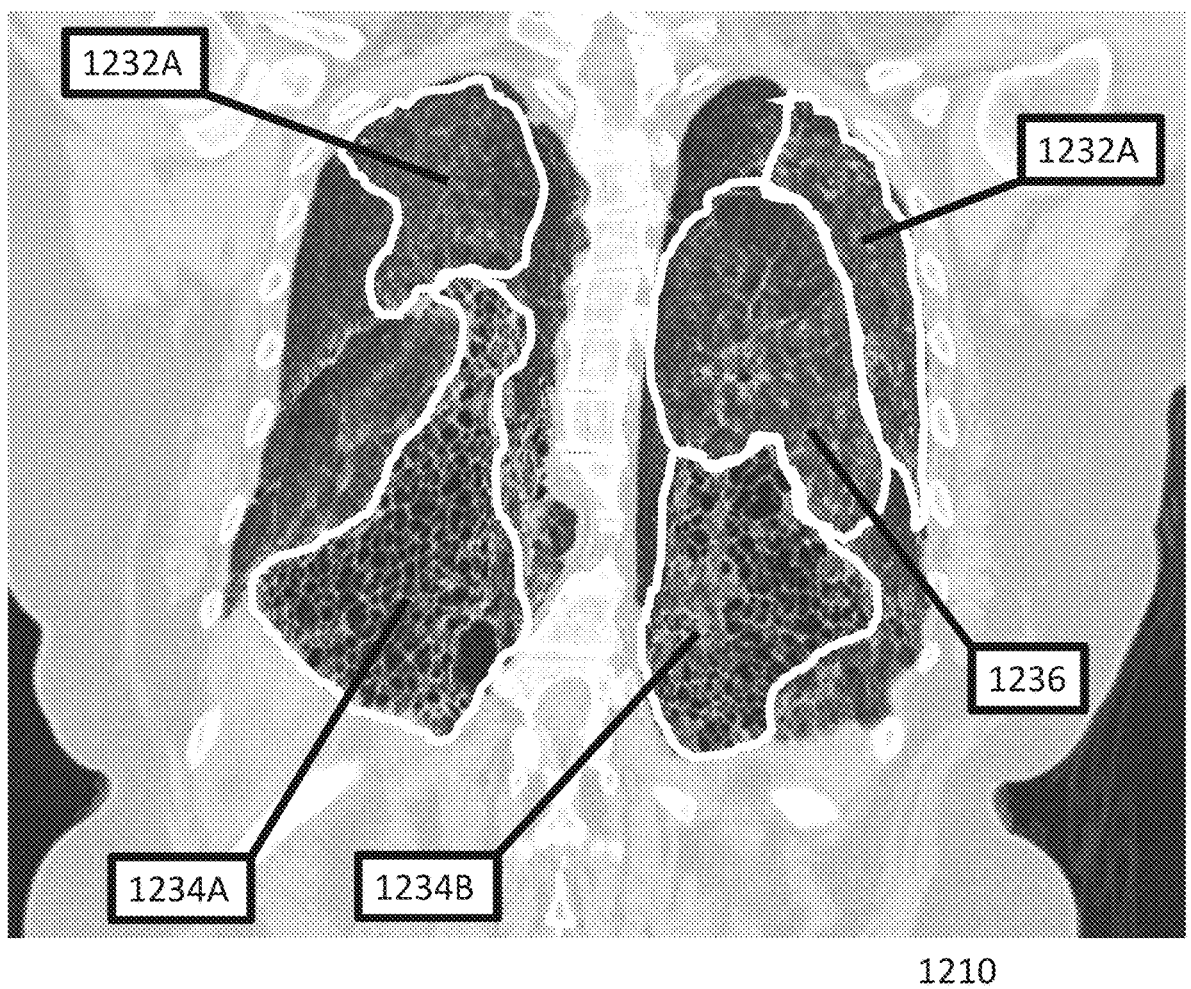
FIG. 12 illustrates an example of selected sub-pleural region of a patient's lungs with annotations according to an aspect of the present disclosure.

Additional information may be provided in addition to the display images as discussed herein. In some embodiments, meta data (e.g. patient information, lung size, the time/date, etc.) may be presented to a physician in addition to the display images. Furthermore, various attributes of the anatomical structure of interest, or other portions of the display image may be annotated. As shown in FIG. 12, various portions of a display image (e.g. display image 1210) may be annotated based on the type or severity of disease. As shown, FIG. 12 comprises a few annotations (e.g. annotations 1232-1236) representing lung features, such as various lung textures, disease phenotypes, and the like. With respect to FIG. 12, annotations 1232A, 1232B may represent a portion of the lungs comprising a reticulation texture, annotations 1234A, 1234B may represent a portion of the lungs comprising a honeycombing texture, and annotation 1236 may represent a portion of the lungs comprising a ground glass texture. In some embodiments, the annotations may comprise visual outlines and/or labels as shown in FIG. 12. Additionally or alternatively, annotations may comprise a variety of other features, such as various colors, masks, or the like.

Figure 13:
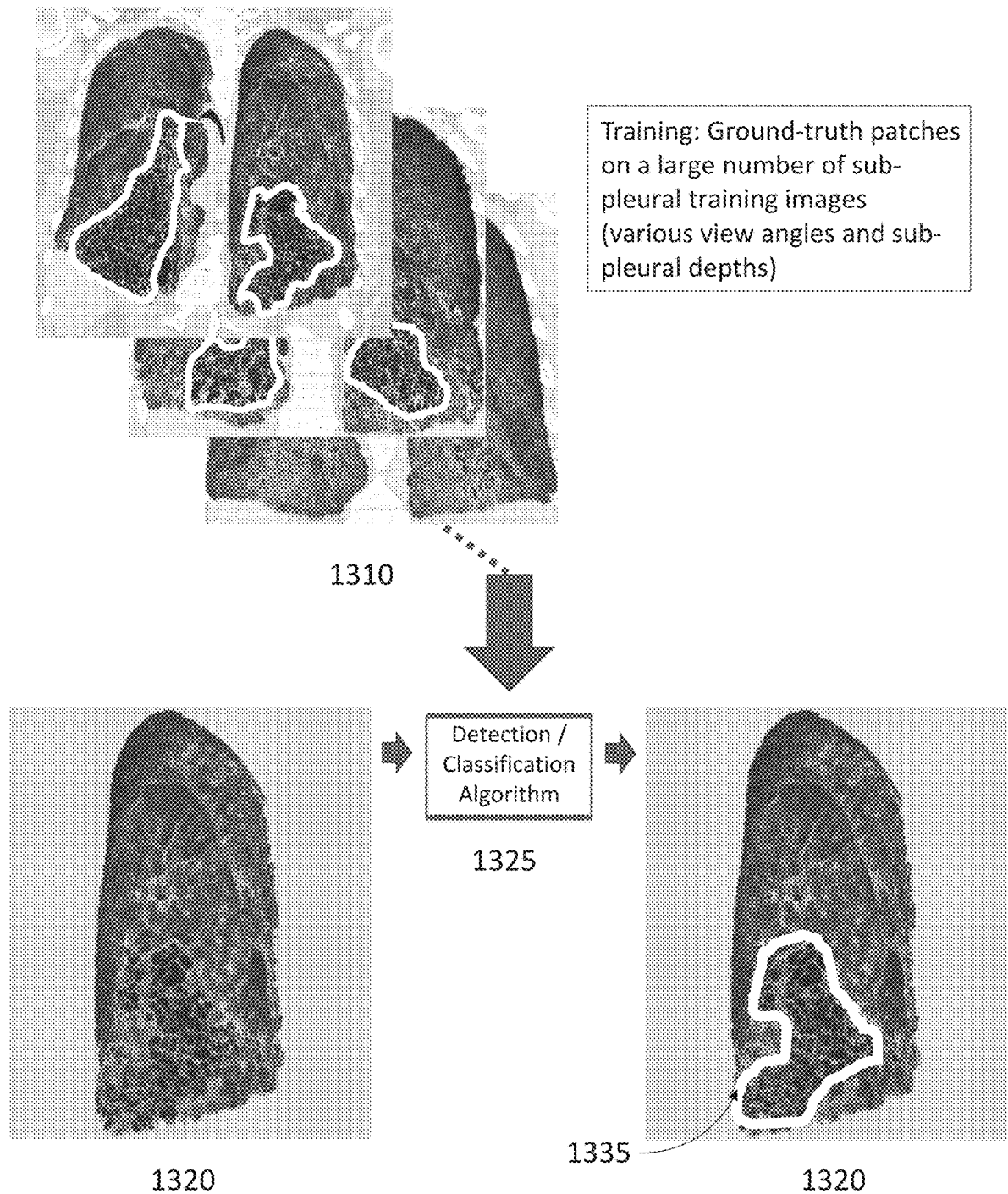
FIG. 13 illustrates a schematic diagram of classifying and detecting regions in various display images that exhibit one or more disease characteristics of interest by using a database comprising various datasets.

In some embodiments, the type, severity, or characteristic of disease may be determined by a physician and then labelled on the display image accordingly. Additionally or alternatively, the type of disease, severity of disease, characteristic of disease or the like may be detected and/or classified automatically. FIG. 13 provides a schematic showing how a database comprising various datasets can be used to classify and detect regions in various display images that exhibit one or more disease characteristics of interest. In some embodiments, the datasets may comprise texture and other training samples annotated at various view angle, sub-pleural depths, or the like using the sub-pleural display. As shown, a plurality of datasets 1310 can be expertly annotated in a training step. Then an unlabeled display image and/or data set, such as display image 1320 may be analyzed using an algorithm 1325 (e.g. a machine learning algorithm) trained on a database comprising the plurality of datasets 1310 to detect and/or classify various features within the received display image 1320 and then automatically annotate any disease characteristics of interest. As shown, the features present in the lower left-hand corner of display image 1320 may be determined to be a patch containing one or more disease characteristics of interest. Accordingly, display image 1320 may be annotated via annotation 1335 to illustrate the presence of a disease characteristic patch. In some embodiments, annotations may be visual annotations overlaid on the display image. Additionally or alternatively other annotations may be used, such as tags in metadata, palletization of the image, or the like.

Various embodiments have been described. Such examples are non-limiting, and do not define or limit the scope of the invention in any way. Additional embodiments described with the respect to the invention are listed below:

The invention claimed is:

1. A method for visualizing sub-pleural regions of an anatomical structure of interest from a set of volumetric data comprising:
   receiving the set of volumetric data representative of the anatomical structure of interest, wherein:
   the volumetric data representative of the anatomical structure of interest comprises:
      volumetric data representative of an outer surface of the anatomical structure of interest; and
      volumetric data representative of each of a plurality of sub-pleural regions of the anatomical structure of interest, the volumetric data representative of each of the plurality of sub-pleural regions being a region of the volumetric data representative of the anatomical structure of interest which is distant from the outer surface by a corresponding sub-pleural depth;
   determining a first sub-pleural depth;
   determining a first sub-pleural region of the plurality of sub-pleural regions of the anatomical structure of interest based on the determined first sub-pleural depth, the first sub-pleural region being distant from the outer surface of the anatomical structure of interest by the first sub-pleural depth;
   based on the determined first sub-pleural region, extracting, from the set of volumetric data, the volumetric data representative of the first sub-pleural region; and
   rendering a display image based upon the extracted volumetric data representative of the first sub-pleural region.

2. The method of claim 1, wherein determining the first sub-pleural depth region-comprises receiving a first depth value.

3. The method of claim 2, wherein receiving the first depth value comprises receiving a selection of the first depth value from a physician via a user interface.

4. The method of claim 2, wherein the first depth value is selectable from a plurality of depth values.

5. The method of claim 1, further comprising presenting the display image to a physician via a display.

6. The method of claim 5, further comprising:
   determining one or more additional features; and
   presenting the one or more additional features along with the display image.

7. The method of claim 6, wherein the one or more additional features comprises
   one or more of disease phenotype and disease severity for one or more locations of the
   displayed portions of the anatomical structure of interest.

8. The method of claim 6, further comprising:
   receiving a plurality of datasets, each of the plurality of datasets comprising volumetric images with known disease phenotypes and/or disease severity; and
   determining the one or more additional features comprises:
      comparing the volumetric data representative of the first sub-pleural region to the received plurality of datasets; and
      classifying disease phenotypes and/or disease severity in the first sub-pleural region based on the comparisons with the received plurality of datasets.

9. The method of claim 8, wherein comparing the volumetric data representative of the first sub-pleural region to the received plurality of datasets comprises using a training algorithm.

10. The method of claim 9, wherein the training algorithm is configured to recognize characteristics present in the volumetric data representative of the first sub-pleural region based on characteristics present in the plurality of datasets.

11. A non-transitory computer readable medium programmed with instructions to cause one or more processors to:
   receive a set of volumetric data representative of an anatomical structure of interest comprising volumetric data representative of an outer surface of the anatomical structure of interest and volumetric data representative of each of a plurality of sub-pleural regions of the anatomical structure of interest, the volumetric data representative of each of the plurality of sub-pleural regions being a region of the volumetric data representative of the anatomical structure of interest which is distant from the outer surface by a corresponding sub-pleural depth;
   determine a first sub-pleural depth;
   determine a first sub-pleural region of the plurality of sub-pleural regions of the anatomical structure of interest based on the determined first sub-pleural depth, the first sub-pleural region being distant from the outer surface of the anatomical structure of interest by the first sub-pleural depth;
   based on the determined first sub-pleural region, extract, from the set of volumetric data, the volumetric data representative of the first sub-pleural region; and
   render a display image based upon the extracted volumetric data representative of the first sub-pleural region.

12. The non-transitory computer readable medium of claim 11, wherein the one or more processors are further caused to render a plurality of display images.

13. The non-transitory computer readable medium of claim 12,
   wherein the set of volumetric data includes volumetric data taken at different points in time, and wherein the plurality of display images comprises display images of the anatomical structure of interest taken at the different points in time.

14. The non-transitory computer readable medium of claim 12,
   wherein the plurality of display images comprises display images based upon extracted volumetric data representative of a plurality of different sub-pleural regions of the anatomical structure of interest.

15. The non-transitory computer readable medium of claim 12,
   wherein the plurality of display images comprises display images rendered at a plurality of viewing directions from the set of volumetric data.

16. A system, for visualizing sub-pleural regions of an anatomical structure, the system comprising:
   a memory, the memory configured to store volumetric data; and
   a processor, the processor configured to:
      receive a set of volumetric data representative of an anatomical structure of interest, wherein the anatomical structure of interest comprises an outer surface and a plurality of sub-pleural regions, each of the plurality of sub-pleural regions being a region of the anatomical structure of interest which is distant from the outer surface by a corresponding sub-pleural depth and wherein the volumetric data representative of the anatomical structure of interest comprises volumetric data representative of the outer surface and volumetric data representative of each of the plurality of sub-pleural regions;

determine a first subpleural depth;

determine a first sub-pleural region of the plurality of sub-pleural regions of the anatomical structure of interest, the first sub-pleural region being distant from the outer surface of the anatomical structure of interest by the first sub-pleural depth;

based on the determined first sub-pleural region, extract, from the set of volumetric data, the volumetric data representative of the first sub-pleural region; and render a display image based upon the extracted volumetric data representative of the first sub-pleural region.

17. The system of claim 16, wherein rendering the display image further comprises projecting the volumetric data representative of the first sub-pleural region onto the display image.

18. The system of claim 16, wherein the anatomical structure of interest comprises at least one lung.

19. The system of claim 18, wherein the outer surface comprises at least one of a lung pleurae or a visceral pleura.

20. The system of claim 16, wherein each of the plurality of sub-pleural regions is a region which is offset from the surface of the anatomical structure of interest by the corresponding sub-pleural depth in an offset direction normal to the surface of the anatomical structure based on a three-dimensional model of the anatomical structure of interest.

\* \* \* \* \*